United States Patent
Ralston et al.

(10) Patent No.: US 11,137,486 B2
(45) Date of Patent: Oct. 5, 2021

(54) PARAMETER LOADER FOR ULTRASOUND PROBE AND RELATED APPARATUS AND METHODS

(71) Applicant: Butterfly Network, Inc., Guilford, CT (US)

(72) Inventors: Tyler S. Ralston, Clinton, CT (US); Andrew J. Casper, Clinton, CT (US); Nevada J. Sanchez, Guilford, CT (US)

(73) Assignee: BFLY Operations, Inc., Guilford, CT (US)

( * ) Notice: Subject to any disclaimer, the term of this patent is extended or adjusted under 35 U.S.C. 154(b) by 759 days.

(21) Appl. No.: 15/517,211

(22) PCT Filed: Oct. 7, 2015

(86) PCT No.: PCT/US2015/054422
§ 371 (c)(1),
(2) Date: Apr. 6, 2017

(87) PCT Pub. No.: WO2016/057631
PCT Pub. Date: Apr. 14, 2016

(65) Prior Publication Data
US 2017/0307740 A1   Oct. 26, 2017

Related U.S. Application Data

(60) Provisional application No. 62/061,613, filed on Oct. 8, 2014.

(51) Int. Cl.
*G01S 7/52* (2006.01)
*A61B 8/00* (2006.01)
(Continued)

(52) U.S. Cl.
CPC .............. *G01S 7/5208* (2013.01); *A61B 8/44* (2013.01); *A61B 8/4411* (2013.01);
(Continued)

(58) Field of Classification Search
CPC combination set(s) only.
See application file for complete search history.

(56) References Cited

U.S. PATENT DOCUMENTS 6,475,146 B1 * 11/2002 Frelburger ........... A61B 5/0002
600/437
7,549,961 B1    6/2009 Hwang
(Continued)

FOREIGN PATENT DOCUMENTS

CN    1361871 A    7/2002
CN    1766672 A    5/2006
(Continued)

OTHER PUBLICATIONS

European Communication dated Mar. 15, 2021 in connection with European Application No. 15849729.7.
(Continued)

*Primary Examiner* — Henry Tsai
*Assistant Examiner* — Christopher A Bartels
(74) *Attorney, Agent, or Firm* — Wolf, Greenfield & Sacks, P.C.

(57) ABSTRACT

Programmable ultrasound probes and methods of operation are described. The ultrasound probe may include memory storing parameter data and may also include a parameter loader which loads the parameter data into programmable circuitry of the ultrasound probe. In some instances, the ultrasound probe may include circuitry grouped into modules which may be repeatable and which may be coupled together to allow data to be exchanged between the modules.

19 Claims, 8 Drawing Sheets

(51) Int. Cl.
*H04B 11/00* (2006.01)
*H04L 5/00* (2006.01)
*H04L 12/24* (2006.01)
*H04L 29/08* (2006.01)

(52) U.S. Cl.
CPC .............. *A61B 8/4472* (2013.01); *A61B 8/54* (2013.01); *A61B 8/565* (2013.01); *G01S 7/52082* (2013.01); *H04B 11/00* (2013.01); *H04L 5/0048* (2013.01); *H04L 41/0803* (2013.01); *H04L 69/324* (2013.01)

(56) References Cited

U.S. PATENT DOCUMENTS

| | | | |
|---|---|---|---|
| 7,984,651 B2* | 7/2011 | Randall | A61B 8/4483 73/661 |
| D657,361 S | 4/2012 | Goodwin et al. | |
| 8,277,380 B2 | 10/2012 | Daft et al. | |
| 8,647,279 B2 | 2/2014 | Daft et al. | |
| 8,852,103 B2 | 10/2014 | Rothberg et al. | |
| 9,229,097 B2 | 1/2016 | Rothberg et al. | |
| 9,521,991 B2 | 12/2016 | Rothberg et al. | |
| 9,592,030 B2 | 3/2017 | Rothberg et al. | |
| 9,592,032 B2 | 3/2017 | Rothberg et al. | |
| 2003/0018260 A1* | 1/2003 | Erikson | A61B 8/4483 600/447 |
| 2003/0097071 A1 | 5/2003 | Halmann et al. | |
| 2003/0176787 A1 | 9/2003 | Gilbert et al. | |
| 2004/0267126 A1 | 12/2004 | Takeuchi | |
| 2006/0092930 A1* | 5/2006 | Shah | H04L 67/125 370/389 |
| 2006/0241425 A1* | 10/2006 | Payne | A61B 8/02 600/437 |
| 2007/0242567 A1 | 10/2007 | Daft et al. | |
| 2008/0137482 A1 | 6/2008 | Kang et al. | |
| 2010/0245066 A1 | 9/2010 | Sarioglu et al. | |
| 2011/0055447 A1 | 3/2011 | Costa | |
| 2011/0319765 A1* | 12/2011 | Gertner | A61N 7/02 600/453 |
| 2012/0113759 A1 | 5/2012 | Oshiki et al. | |
| 2012/0179044 A1* | 7/2012 | Chiang | A61B 8/145 600/447 |
| 2012/0226161 A1 | 9/2012 | Pelissier et al. | |
| 2012/0271166 A1* | 10/2012 | Shao | G01N 29/348 600/438 |
| 2013/0116561 A1* | 5/2013 | Rothberg | A61B 8/13 600/438 |
| 2013/0324851 A1 | 12/2013 | Cohen et al. | |
| 2014/0114190 A1 | 4/2014 | Chiang et al. | |
| 2014/0194728 A1* | 7/2014 | Vahala | A61B 8/485 600/411 |
| 2014/0288428 A1* | 9/2014 | Rothberg | G01S 7/52034 600/447 |
| 2015/0032002 A1* | 1/2015 | Rothberg | A61B 8/4488 600/440 |
| 2016/0087649 A1* | 3/2016 | Limberg | H04N 21/2383 714/776 |
| 2016/0199030 A1 | 7/2016 | Patil et al. | |
| 2016/0203010 A1* | 7/2016 | Azizian | G06F 9/455 703/23 |
| 2016/0331353 A1* | 11/2016 | Ralston | A61B 8/546 |
| 2017/0151448 A1* | 6/2017 | Yon | A61N 7/02 |
| 2018/0154394 A1* | 6/2018 | Haque | A61B 8/4494 |
| 2020/0188704 A1* | 6/2020 | Barthe | G16H 50/30 |

FOREIGN PATENT DOCUMENTS

| | | |
|---|---|---|
| CN | 101194846 A | 6/2008 |
| CN | 101680948 A | 3/2010 |
| CN | 102215755 A | 10/2011 |
| JP | 2005261593 A | 9/2005 |
| JP | 2006-136711 A | 6/2006 |
| JP | 2012161561 A | 8/2012 |
| WO | WO 00/79300 A1 | 12/2000 |
| WO | WO 2009/077983 A1 | 6/2009 |
| WO | WO 2009/135255 A1 | 11/2009 |
| WO | WO 2013/088196 A1 | 6/2013 |
| WO | WO 2014/151362 A2 | 9/2014 |
| WO | WO 2014/151362 A3 | 11/2014 |

OTHER PUBLICATIONS

PCT/US2015/054422, Feb. 10, 2016, International Search Report and Written Opinion.
PCT/US2015/054422, Apr. 20, 2017, International Preliminary Report on Patentability.
International Search Report and Written Opinion dated Nov. 13, 2014 for Application No. PCT/US2014/032803.
International Search Report and Written Opinion dated Feb. 10, 2016 for Application No. PCT/US2015/054422.
International Preliminary Report on Patentability dated Apr. 20, 2017 for Application No. PCT/US2015/054422.
Daft et al., 5F-3 A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Gurun et al., Front-end CMOS electronics for monolithic integration with CMUT arrays: circuit design and initial experimental results. Proc Ultrason Symp. 2008;390-3.
Extended European Search Report dated May 24, 2018 in connection with European Application No. 15849729.7.
Lewandowski et al., Modular & Scalable Ultrasound Platform with GPU Processing. 2012 IEEE International Ultrasonics Symposium (IUS). IEEE. Oct. 7, 2012; pp. 1-4.
Triger et al., Low-Voltage Coded Excitation Utilizing a Miniaturized Integrated Ultrasound System Employing Piezoelectric 2-D Arrays. IEEE Transactions on Ultrasonics, Ferroelectrics, and Frequency Control. IEEE. Feb. 1, 2010; 57(2):353-362.
European Communiction dated Mar. 15, 2021 in connection with European Application No. 15849729.7.

* cited by examiner

PARAMETER LOADER FOR ULTRASOUND PROBE AND RELATED APPARATUS AND METHODS

CROSS REFERENCE TO RELATED APPLICATIONS

This application is a National Stage Application of PCT/US2015/054422, filed Oct. 7, 2015, which claims the benefit under 35 U.S.C. § 119(e) of U.S. Provisional Patent Application Ser. No. 62/061,613 filed Oct. 8, 2014, and entitled "PARAMETER LOADER FOR ULTRASOUND PROBE AND RELATED APPARATUS AND METHODS," both of which are incorporated herein by reference in their entireties.

BACKGROUND

Field

The present application relates to an architecture and methods for controlling a programmable ultrasound probe.

Related Art

Ultrasound imaging systems typically include an ultrasound probe connected to a host by an analog cable. The ultrasound probe is controlled by the host to emit and receive ultrasound signals. The received ultrasound signals are processed to generate an ultrasound image.

BRIEF SUMMARY

Aspects of the present application relate to a parameter loader for an ultrasound probe, as well as to related apparatus and methods. The ultrasound probe may include programmable digital circuitry allowing for various operating characteristics of the ultrasound probe to be specified one or more times during operation. For example, digital circuitry governing transmit and/or receive operations of the ultrasound probe may be programmed to select characteristics of the waveforms generated, characteristics of signal delays, or characteristics of digital processing performed on received ultrasound signals. In at least some embodiments, a parameter loader is included in the ultrasound probe and is used to store parameter data for programming the digital circuitry of the ultrasound probe as well as to load the parameter data into the digital circuitry.

In some embodiments, the programmable circuitry of the ultrasound probe is arranged into like modules coupled together to allow for sharing of parameter data. The parameter loader may provide the parameter data to one or more of the ultrasound modules, which may act upon the parameter data and/or pass the parameter data to other ultrasound modules of the ultrasound probe. Such a configuration may facilitate scaling of the ultrasound probe to larger numbers of modules, may simplify design of the circuitry of the ultrasound probe by focusing the design at a modular level rather than a system level, may provide for efficient communication of data between circuitry of the ultrasound probe, and may reduce the area occupied by the circuitry compared to alternative approaches.

Various aspects of the present application provide methods of operating an ultrasound probe and a parameter loader of the ultrasound probe to reduce the amount of parameter data stored on the ultrasound probe and loaded into the programmable digital circuitry of the ultrasound probe. For instance, redundancies in parameter data among multiple circuit components may be exploited to reduce the data storage and transmission requirements of the ultrasound probe. The redundancies may occur within a single excitation event, for example when multiple circuit components use the same parameter values during the excitation event, and/or across multiple excitation events.

According to an aspect of the present application, an apparatus is described, comprising an ultrasound probe that comprises a plurality of modules including a first module and a second module. Each of the first and second modules comprises transmit circuitry, at least one ultrasound element, and receive circuitry. The first module and second module are coupled to each other and configured to pass parameter data from the first module to the second module.

According to an aspect of the present application an apparatus is provided, comprising an ultrasound probe that comprises programmable circuitry and a memory coupled to the programmable circuitry and configured to store parameter data.

According to an aspect of the present application, a method of providing data to an ultrasound probe is described. The ultrasound probe comprises a plurality of addressable ultrasound modules linked in a daisy-chain configuration. The method comprises creating a packet including both an address of a first ultrasound module of the plurality of addressable ultrasound modules and data, and sending the packet to the plurality of addressable ultrasound modules sequentially.

According to an aspect of the present application, a method of providing data to an ultrasound probe is provided, the probe comprising a plurality of addressable ultrasound modules linked in a daisy-chain configuration. The method comprises creating a packet, and sending the packet to the plurality of addressable ultrasound modules sequentially.

According to an aspect of the present application, a method is described, comprising performing a first acquisition with an ultrasound probe comprising setting digital values for a first ultrasound module of a plurality of ultrasound modules of the ultrasound probe. The method further comprises performing a second acquisition with the ultrasound probe, the second acquisition comprising setting, for a second ultrasound module of the plurality of ultrasound modules, the digital values set for the first ultrasound module during the first acquisition.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1A:
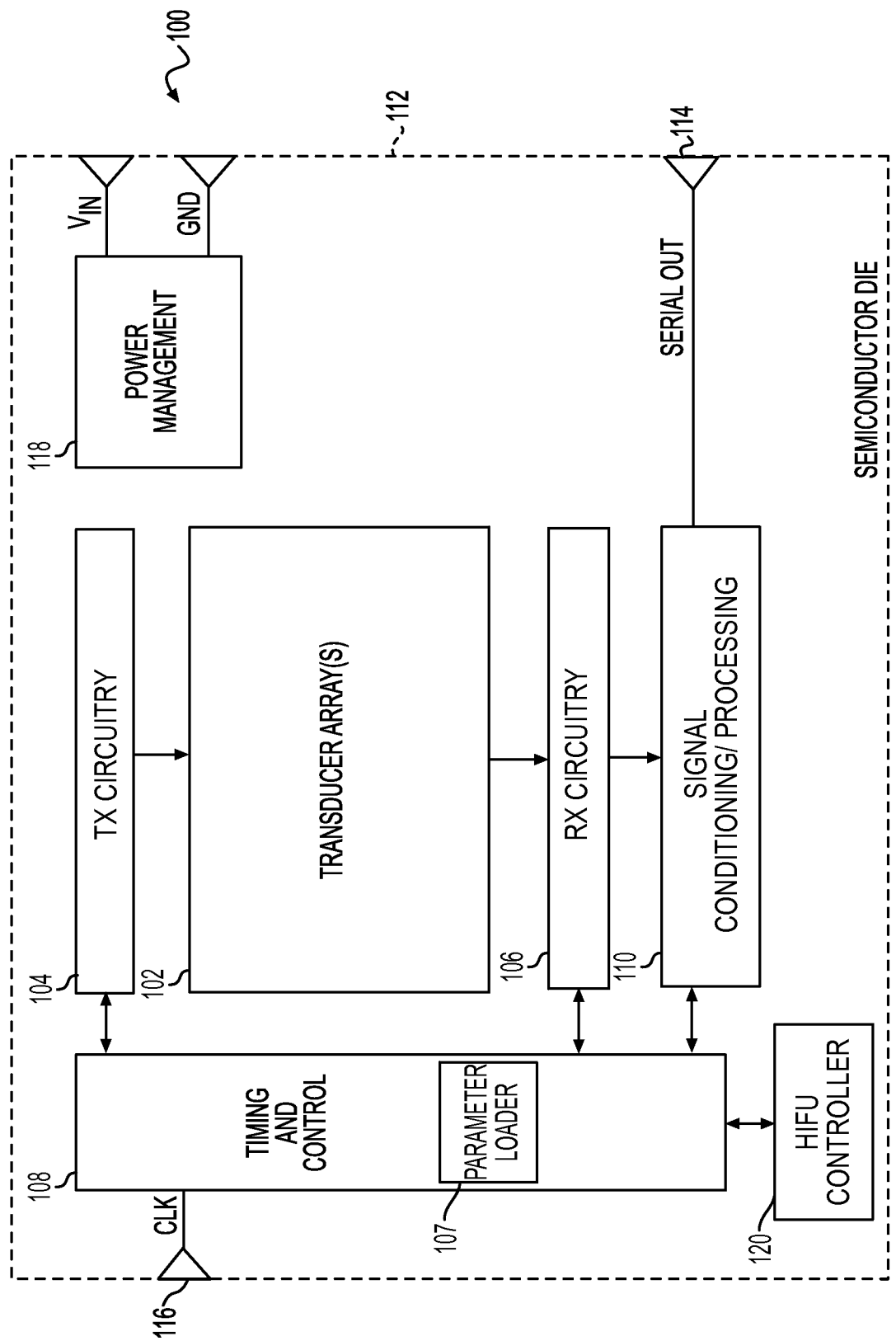
FIG. 1A illustrates an example of an ultrasound probe which may include a parameter loader and which may implement aspects described herein.

Aspects of the present application are directed to an ultrasound probe parameter loader and methods for loading parameter data onto a programmable ultrasound probe and for communicating the parameter data between components of the ultrasound probe. These aspects arise from, but are not limited by, a desire to provide a programmable ultrasound probe capable of performing a variety of complex imaging functions while being connectable to a host via a commercially-available digital connection. Compared to some ultrasound systems which place most, if not all, control, transmit, and receive circuitry in the host, it is desirable to have an ultrasound probe that contains the control, transmit, and receive circuitry, or at least some of those components. Including such components on the ultrasound probe facilitates the ability to connect the probe to a variety of hosts (for example, a laptop computer or personal digital assistant (PDA)) via a relatively simple, digital connection, differing from the complex and costly analog cables typically used to connect conventional ultrasound probes to a host. This, in turn, increases accessibility of ultrasound technology beyond that afforded by the relatively complex and costly conventional systems.

To achieve a versatile ultrasound probe capable of performing medically relevant ultrasound imaging in terms of, for example, supporting multiple ultrasound imaging modes with high resolution and frame rates, the probe may be configured with programmable circuitry. The programmable circuitry may include control, transmit, and/or receive circuitry, and the programmable nature may afford control over operating features such as the imaging mode used and the types of processing performed on ultrasound signals received by the ultrasound probe. While such programmability is beneficial in terms of the capabilities provided to the ultrasound probe, a potential problem also arises in terms of the need to provide the programming data to the ultrasound probe at a time and in a manner which does not negatively impact performance, and which accounts for the types of connections described previously for allowing connection of the ultrasound probe to a variety of hosts.

While one approach for providing such data to a programmable ultrasound probe is to send each piece of data from the host to the ultrasound probe whenever needed, Applicant has appreciated that such a brute force technique is impractical, for instance because it will not scale as ultrasound probes increase in the number of transducing elements and resolution. Thus, aspects of the present application provide structures and methods which facilitate intelligent and efficient loading of parameter data onto an ultrasound probe, as well as providing for efficient communication of the parameter data on the ultrasound probe.

According to an aspect of the present application, an ultrasound probe includes programmable circuitry and a memory which stores parameter data for programming the programmable circuitry of the ultrasound probe. The parameter data stored in the memory of the ultrasound probe may represent all the data needed to program the programmable circuitry of the ultrasound probe in some embodiments, but in other embodiments the memory of the ultrasound probe stores only a subset of the parameter data needed and additional parameter data may be stored in a separate memory, such as in a host. A parameter loader is also included in the ultrasound probe in some embodiments, and operates to load the parameter data from the memory of the ultrasound probe into the programmable circuitry.

According to an aspect of the present application, parameter data is loaded onto an ultrasound probe and re-used for multiple acquisition events. Applicant has appreciated that certain parameter data used to program the programmable circuitry of an ultrasound probe may be common to multiple imaging modes and acquisitions, and thus that efficient operation of the ultrasound probe may be facilitated by storing certain parameter data on the ultrasound probe and re-using it in multiple imaging modes or acquisitions, rather than loading the same parameter data onto the ultrasound probe repeatedly. In this manner, the amount of data required to be sent from a host to the ultrasound probe may be reduced, which may contribute to achieving desirable frame rates, reducing data storage requirements, and increasing communication efficiency with a host, among other operating characteristics.

According to an aspect of the present application, the circuitry of a programmable ultrasound probe is grouped into repeatable modules coupled together in a manner which facilitates data communication between the modules. According to an aspect of the application, the repeatable modules are arranged in an array. For example, the ultrasound modules may be coupled in a daisy-chain configuration (or ring network) and may operate to pass data from one ultrasound module to the next, although it should be appreciated that a daisy-chain configuration is only one non-limiting example of a linear array configuration, and that other array configurations may be used. The modules may be repeatable in that they may be identical or at least substantially the same. The circuitry of the modules may include control circuitry, transmit circuitry and/or receive circuitry. Use of repeatable circuitry modules may facilitate scaling of the ultrasound probe (by adding more identical or substantially identical modules) and may also increase efficient communication of data between circuitry, as described in greater detail below.

According to an aspect of the present application, a programmable ultrasound probe is controlled using data packets and data packet-based communication techniques. In some embodiments, the ultrasound probe includes circuitry grouped into addressable modules which may include, for example, transmit and receive circuitry. Packets of data may be sent to the ultrasound modules and may include an address identifying one or more of the ultrasound modules. The ultrasound module(s) having the address identified by the packet(s) may operate on such packet(s) while those ultrasound modules not matching the address of the packet(s) may pass the packet(s) to another ultrasound module.

In some embodiments the ultrasound probe is an ultrasound on a chip probe incorporating one or more of the aspects described above. The ultrasound probe may include ultrasonic transducers and programmable circuitry, such as programmable transmit and/or receive circuitry. The programmable circuitry of the ultrasound probe may be included on the same substrate as the ultrasonic transducers in some embodiments, or on a separate substrate in alternative embodiments.

Aspects of the present application relate to manufacturing ultrasound probes and circuitry of the types described herein. For example, manufacturing an ultrasound probe may comprise forming a parameter loader and memory on the ultrasound probe. The parameter loader and memory may be formed on a same substrate as a plurality of ultrasonic transducers of the ultrasound probe, or may be formed on separate substrates in some embodiments.

The aspects and embodiments described above, as well as additional aspects and embodiments, are described further below. These aspects and/or embodiments may be used individually, all together, or in any combination of two or more, as the application is not limited in this respect.

To provide context and facilitate explanation of the various aspects of the present application, a specific example of an ultrasound probe is now described together with specific examples of parameters which may be applicable in such a probe. Yet, it should be appreciated that aspects of the present application apply more broadly than the specific ultrasound probe and ultrasound parameters now described.

Referring to FIG. 1A, the ultrasound probe 100 includes one or more transducer arrangements (e.g., arrays) 102 of ultrasonic transducers, transmit (TX) circuitry 104, receive (RX) circuitry 106, a timing and control circuit 108, a signal conditioning/processing circuit 110, and/or a power management circuit 118 receiving ground (GND) and voltage reference ($V_{IN}$) signals. The ultrasound probe 100 may include a parameter loader 107 for loading parameters into the other circuitry of the ultrasound probe, as will be described in greater detail below with respect to FIG. 5. The parameter loader 107 may be part of the timing and control circuit 108, or may be separate in other embodiments. In general, the timing and control circuit 108 may include suitable circuitry for controlling operation of the transmit circuitry 104 and receive circuitry 106. Optionally, a high intensity focused ultrasound (HIFU) controller 120 may be included if the ultrasound probe 100 is to be used to provide HIFU.

In the embodiment shown in FIG. 1A, all of the illustrated components are formed on a single semiconductor die (or substrate or chip) 112, and thus the illustrated embodiment is an example of an ultrasound on a chip device. However, not all embodiments are limited in this respect. In addition, although the illustrated example shows both TX circuitry 104 and RX circuitry 106, in alternative embodiments only TX circuitry or only RX circuitry may be employed. For example, such embodiments may be employed in a circumstance in which the ultrasound probe is operated as a transmission-only device to transmit acoustic signals or a reception-only device used to receive acoustic signals that have been transmitted through or reflected by a subject being ultrasonically imaged, respectively.

The ultrasound probe 100 further includes a serial output port 114 to output data serially to a host. The ultrasound probe 100 may also include a clock input port 116 to receive and provide a clock signal CLK to the timing and control circuit 108.

Figure 1B:
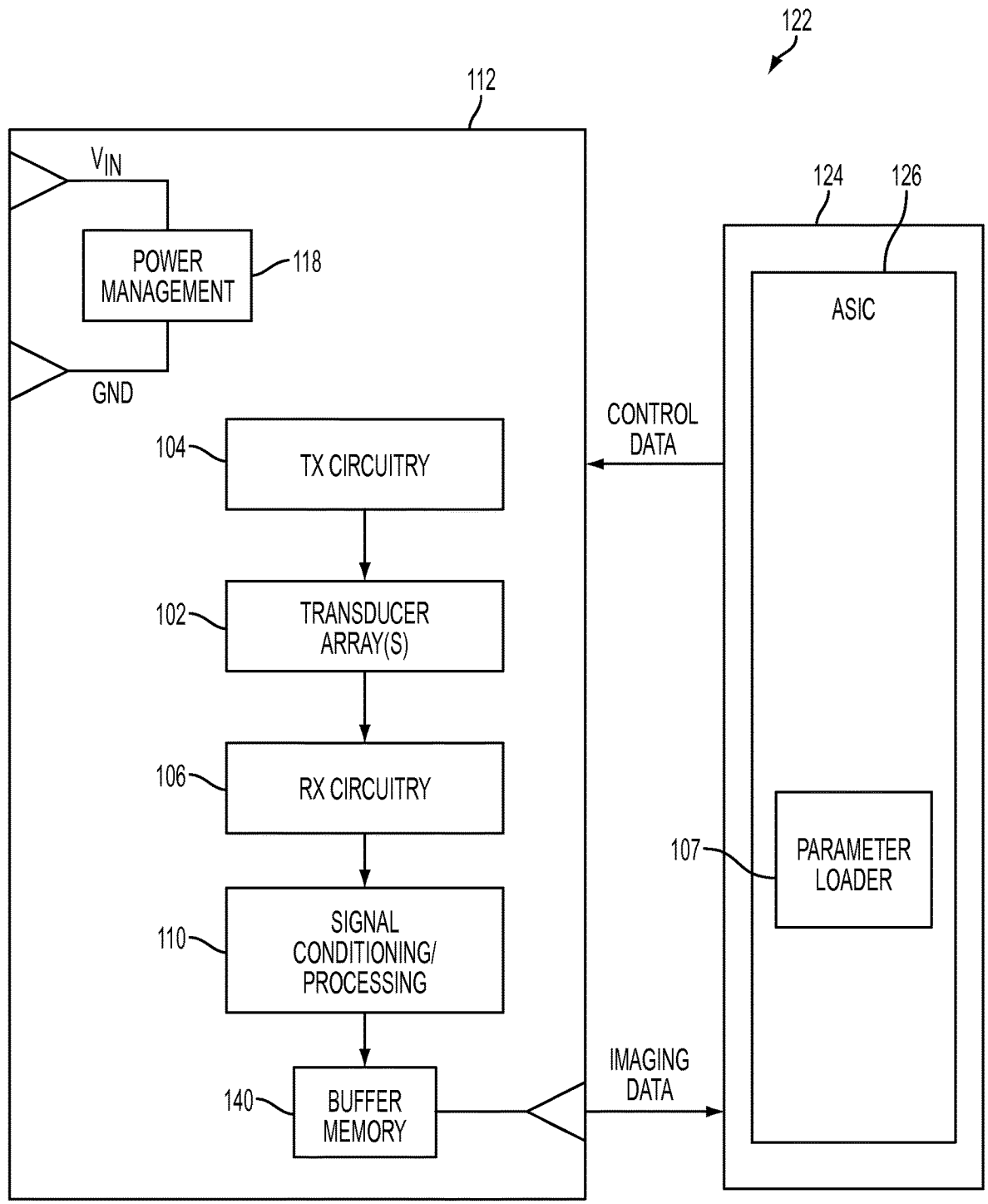
FIG. 1B illustrates a variation of the ultrasound probe of FIG. 1A in which the components of the ultrasound probe are separated among multiple substrates.

FIG. 1B illustrates an embodiment in which the components of the ultrasound probe are divided among two substrates as an alternative to the configuration of FIG. 1A. As shown, the ultrasound probe 122 includes a second substrate 124 on which an application specific integrated circuitry (ASIC) 126 is disposed or formed. An example of the ASIC 126 is described further below in connection with FIG. 5 and may, for example, include the parameter loader 107. Control data including parameter data may be sent by the ASIC 126 to the components on the semiconductor die 112 and imaging data, as an example, may be sent from the signal conditioning/processing circuitry 110 to the ASIC 126. In some embodiments, an optional buffer memory 140 is included on the semiconductor die 112 and the imaging data passes through the buffer memory 140 on its way to the ASIC 126.

Figure 2:
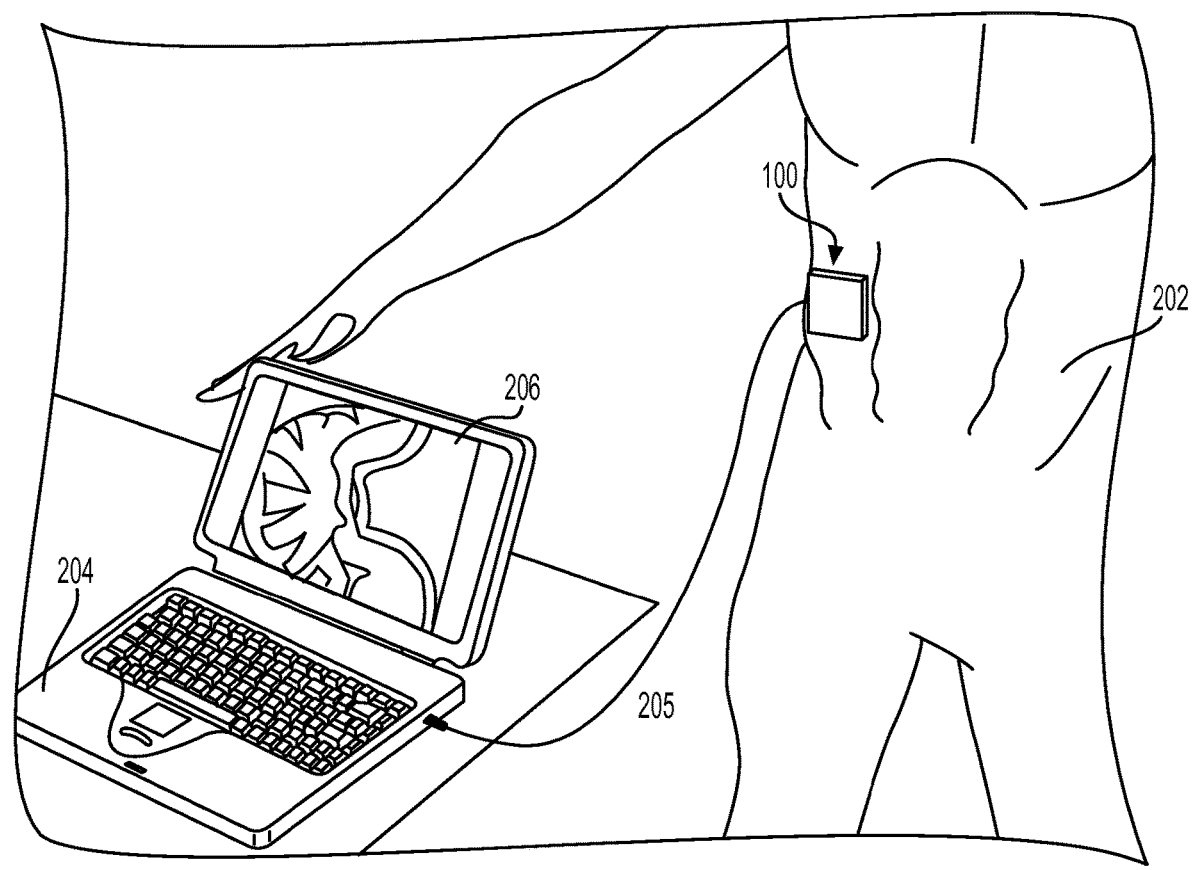
FIG. 2 illustrates an example of an ultrasound probe coupled to a host.

FIG. 2 illustrates an example of the manner in which an ultrasound probe may connect to a host, as well as an example of the host. The ultrasound probe 100 is shown for purposes of illustration as being used to investigate a subject 202. The ultrasound probe 100 may be coupled to the host 204 via a connection 205, which in the illustrated example is a wired connection and which may connect to the serial output port 114 and clock input port 116 of the ultrasound probe 100 (shown in FIG. 1A). The connection 205 may be a digital connection, for example being of a type commonly used with commercial digital electronics, such as a universal serial bus (USB) cable, Thunderbolt, or FireWire. In some embodiments, the connection 205 may be wireless, for example being a Bluetooth® connection, although alternative wireless connections may be used for short and/or long range communication. The host 204 may be a computer (e.g., a laptop computer as shown or a desktop computer), a personal digital assistant, a smartphone, a tablet, or other computing device, and may include the display screen 206 on which ultrasound images may be displayed.

Figure 3:
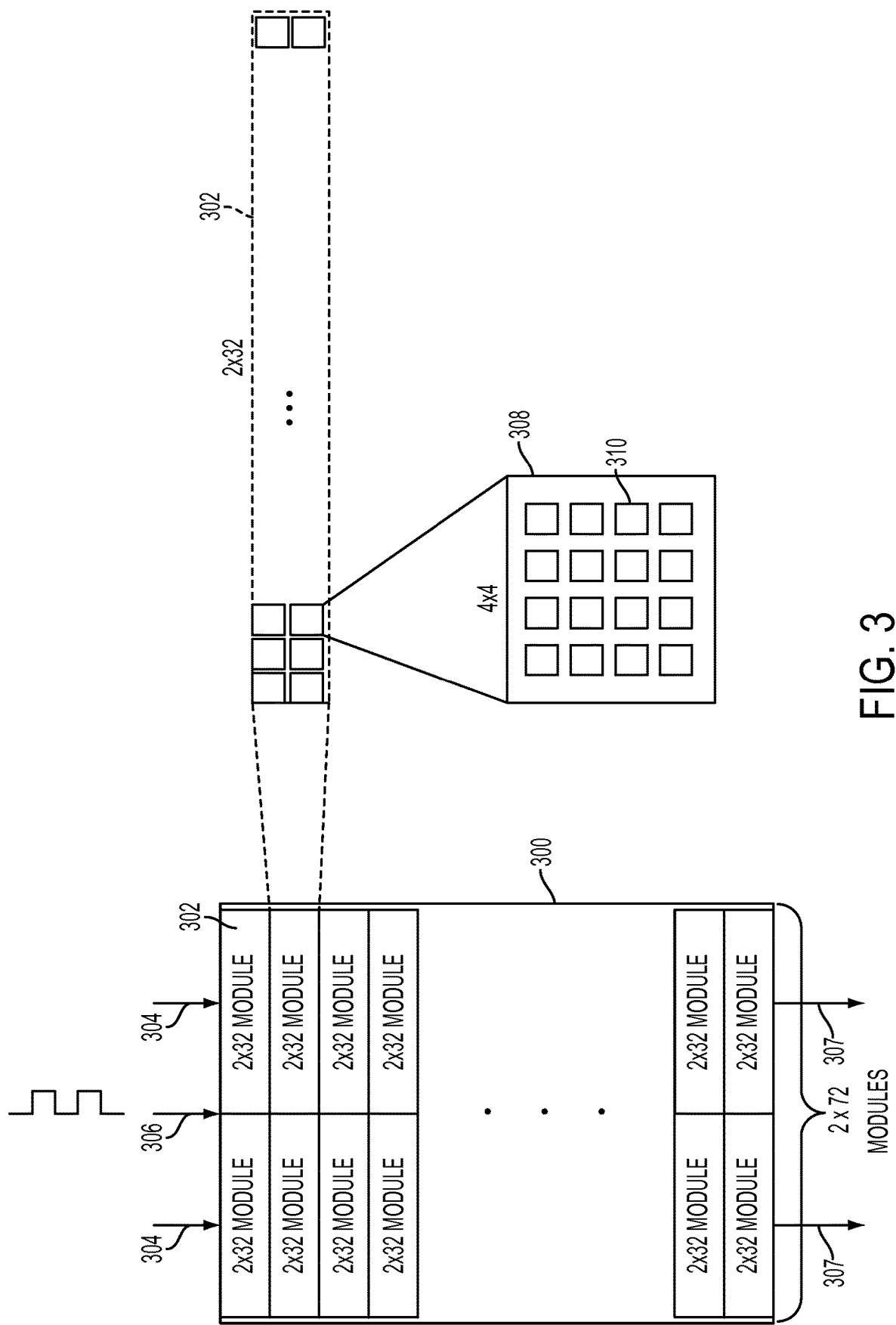
FIG. 3 illustrates an example of an ultrasound probe having a plurality of like ultrasound modules coupled together and including programmable circuitry.

As described previously, an ultrasound probe according to an aspect of the present application includes circuitry arranged in a modular configuration. An example is illustrated in FIG. 3, representing a non-limiting implementation of the ultrasound probe 100 of FIG. 1A.

The ultrasound probe 300 includes a plurality of ultrasound modules 302 arranged in two rows (or columns, depending on orientation). In this non-limiting example, there are 72 such ultrasound modules per row, giving a total of 144 such ultrasound modules 302 for the ultrasound probe 300. In this example, the ultrasound modules are identical to each other, each including transmit circuitry, ultrasound transducers, and receive circuitry. In the illustrated non-limiting example, the ultrasound modules 302 each include two columns of 32 ultrasound elements 308 for a total of 64 ultrasound elements 308 per ultrasound module 302 as shown in the inset of FIG. 3, and accordingly are referred to herein as 2×32 modules. However, it should be appreciated that the aspects of the present application are not limited to ultrasound modules having any particular number of ultrasound elements, and that a 2×32 module is an example described for purposes of illustration.

The ultrasound modules 302 of each row are coupled such that data (e.g., parameter data) may be transferred from one ultrasound module 302 to a neighboring ultrasound module 302. As described further below in connection with FIG. 4, the coupling may be a daisy-chain configuration (a ring network), although alternatives are possible, such as alternative array configurations. Data 304, such as the parameter data described further below in connection with FIG. 5, is provided to the first ultrasound module 302 of each row of the ultrasound modules 302 and a global clock signal 306 is provided to all the ultrasound modules 302. The global clock signal may be any suitable clock frequency, a non-limiting example of which is 200 MHz. Data out 307 is provided by the ultrasound modules 302, and may represent collected raw data or processed imaging data in some embodiments.

As previously described, an ultrasound module may comprise circuitry in addition to one or more ultrasonic transducers. In some embodiments, an ultrasound module 302 may comprise one or more waveform generators (e.g., two waveform generators, four waveform generators, etc.), encoding circuitry, delay mesh circuitry, and/or decoding circuitry. These examples of circuitry that may be part of an ultrasound module 302 are illustrative and are not limiting, as an ultrasound module may additionally or alternatively comprise any other suitable circuitry.

Ultrasound element 308 may include one or more ultrasonic transducers 310 (also referred to herein as "transducer cells"). Stated differently, ultrasonic transducers 310 may be grouped together to form ultrasound elements 308. In the illustrated embodiment of FIG. 3, each ultrasound element 308 comprises 16 ultrasonic transducers 310 arranged as a two-dimensional array having four rows and four columns. However, it should be appreciated that an ultrasound element 308 may comprise any suitable number of ultrasonic transducers (e.g., one, at least two, at least four, at least 16, at least 25, at least 36, at least 49, at least 64, at least 81, at least 100, between one and 200, more than 200, thousands, etc.).

The ultrasonic transducers 310 may be any suitable type of ultrasonic transducers, including capacitive micromachined ultrasonic transducers (CMUTs) or piezoelectric transducers. CMUTs may be used if the ultrasound probe is to include integrated circuitry and ultrasonic transducers.

While the ultrasound probe 300 includes 144 modules, it should be appreciated that any suitable number of ultrasound modules may be included (e.g., at least two modules, at least ten modules, at least 100 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, etc.). Some of the benefits provided by aspects of the present application are more readily realized as the number of ultrasound modules increases.

Figure 4:
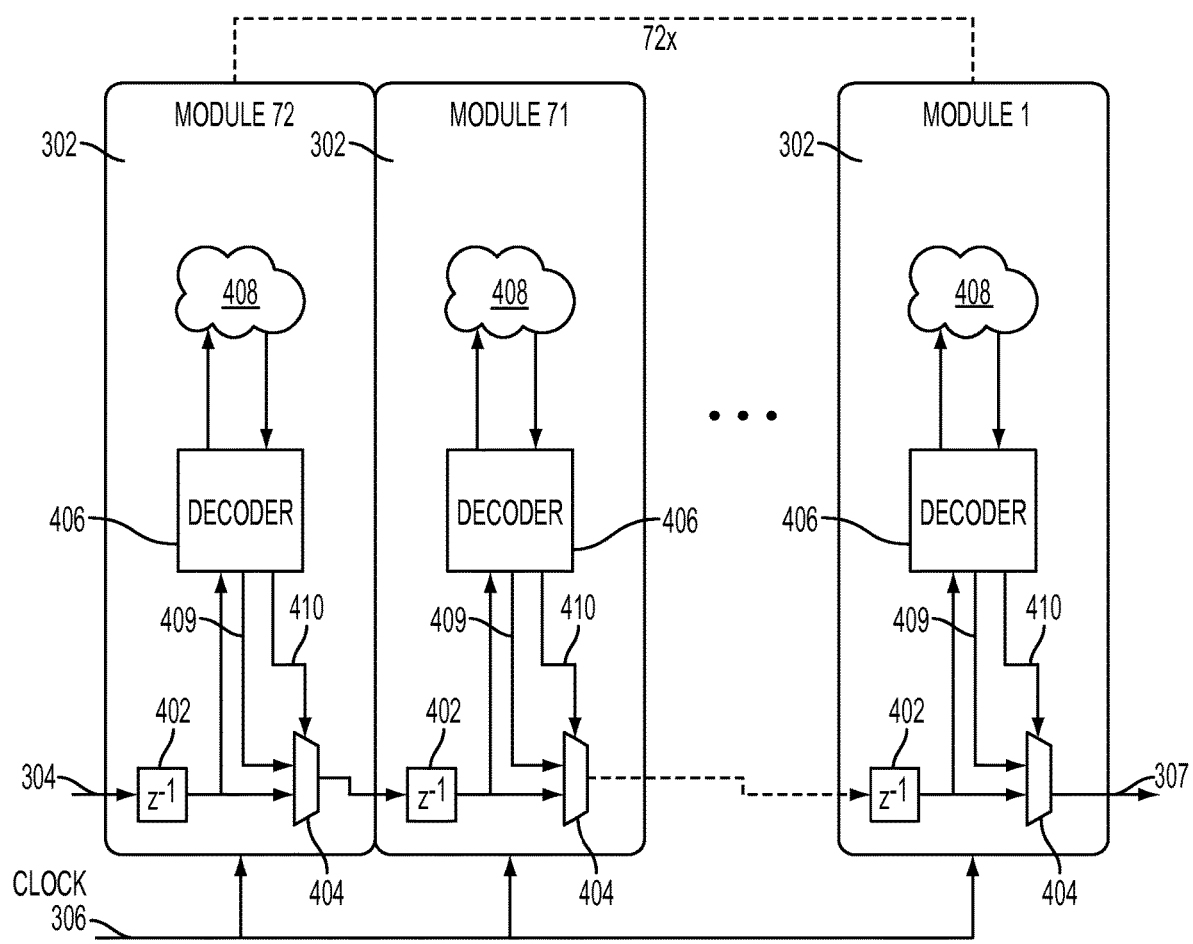
FIG. 4 illustrates a number of the ultrasound modules of the ultrasound probe of FIG. 3 in greater detail and coupled in a daisy-chain configuration.
Figure 5:
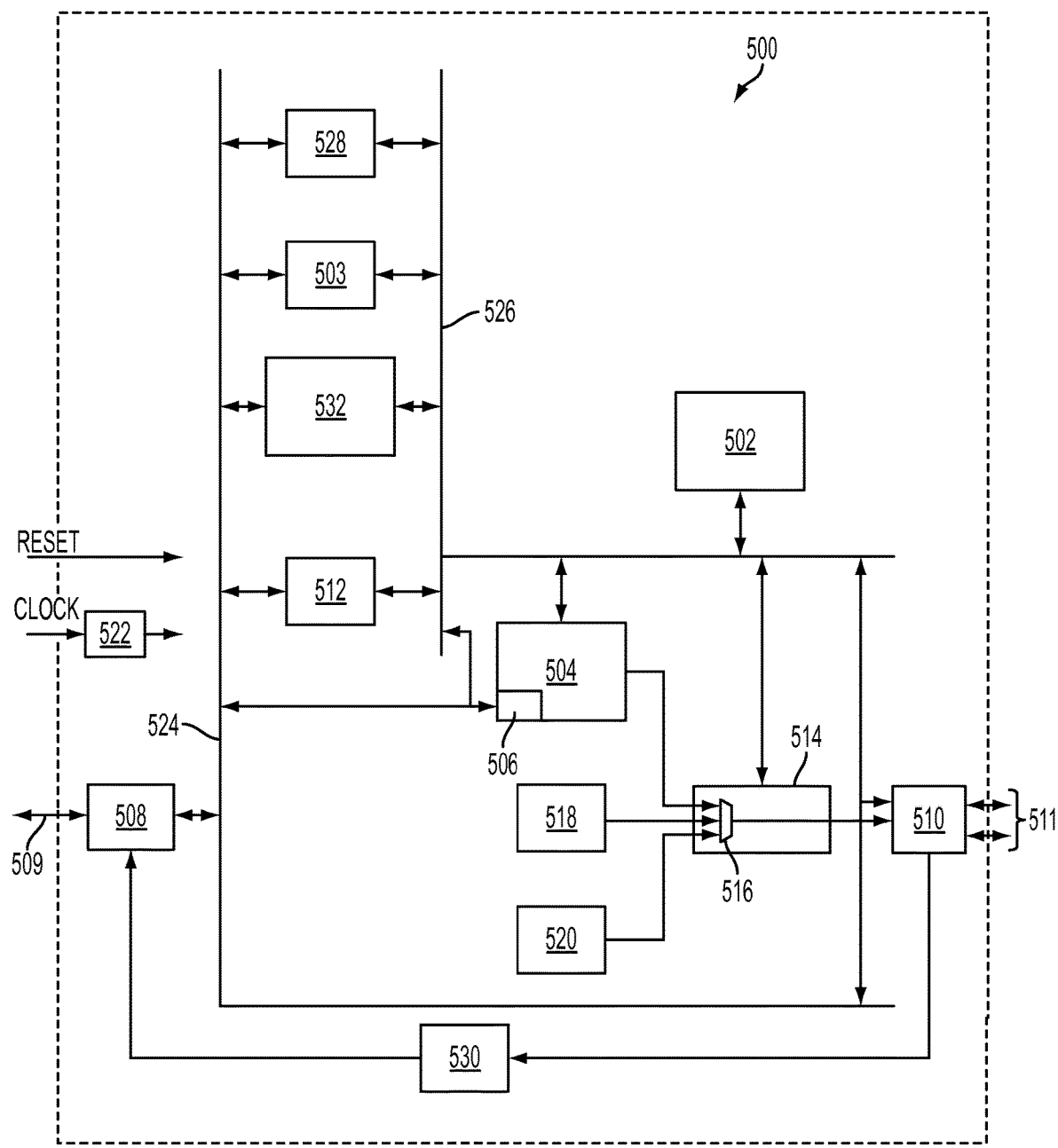
FIG. 5 illustrates an example of a control circuit of an ultrasound probe including a parameter loader configured to load parameter data into programmable circuitry of the ultrasound probe.

FIG. 4 illustrates in greater detail the connection between ultrasound modules 302 of the ultrasound probe 300, focusing on the ultrasound modules 302 from a single row of the ultrasound probe 300. To simplify discussion, the modules 302 are identified as module 72, module 71 . . . module 1. Each ultrasound module 302 includes a shift register 402, a multiplexer 404, and a decoder 406 coupled to the additional circuitry and ultrasound elements 408 of the ultrasound module 302. As shown, the output of the multiplexer 404 of one ultrasound module 302 (e.g., module 72) is coupled to the input of the shift register 402 of the neighboring ultrasound module 302 (e.g., module 71). In this manner, the ultrasound modules 302 are arranged in a daisy-chain to allow data to propagate from one ultrasound module to another (e.g., from module 72 to module 71), although other configurations such as other array configurations may be used.

In operation, the data 304 is provided to a first ultrasound module 302 (e.g., module 72 in this non-limiting example) and, in some scenarios, is then passed from the first ultrasound module 302 to subsequent ultrasound modules in the daisy-chain, as described further below. For example, the data 304 may be provided initially to module 72, from module 72 to module 71, from module 71 to module 70 (not shown), continuing in this manner down to module 1.

According to an aspect of the present application packet-based communication in which data is grouped into packets is implemented by the ultrasound probe. Thus the data 304 may be arranged in packets provided to the ultrasound modules 302. The packets may include an address field, an operation code, and a data field, of any suitable lengths. The packets may include data (e.g., in the data field) related to one or more parameters of operation of the ultrasound probe. In some embodiments, packets specific to a particular type of parameter may be generated, while in other embodiments packets grouping together values of two or more parameters may be generated, for example to group together parameters that relate to a common function (e.g., programming a waveform generator). The latter approach may facilitate efficient communication and simplify the system by not requiring a separate type of packet for each and every parameter type, particularly when the number of controllable parameters is large.

Expanding on the general operation of the ultrasound modules 302 described above, the data 304 may be provided to a first ultrasound module 302 (e.g., module 72) of the ultrasound probe. One of three operations may then occur. The ultrasound module 302 may operate on the data packet and not pass the packet on to subsequent modules. This occurs when the data packet with the data 304 is intended only for the first ultrasound module. Alternatively, the first ultrasound module (e.g., module 72) may pass the data packet on to a subsequent ultrasound module 302 (e.g., module 71) in the daisy-chain without modification. This occurs when the data packet is not intended for the first ultrasound module. As a further option, the first ultrasound module 302 (e.g., module 72) may operate on the data packet, modify it, and then pass it on to a subsequent ultrasound module (e.g., module 71). There are multiple reasons why this may occur, but two examples are described now for illustration.

In some embodiments, the ultrasound modules 302 may have their addresses programmed by a suitable data packet. For example, a data packet may be sent to a first ultrasound module 302 (e.g., module 72) of the ultrasound probe instructing that ultrasound module 302 to set its address to a particular value. The first ultrasound module 302 (e.g., module 72) may do so, but may then modify the data packet by changing the address (e.g., decrementing the address) and sending the modified data packet to the next ultrasound module 302 in the chain (e.g., module 71). The next ultrasound module 302 (e.g., module 71) may receive the modified data packet, set its address according to the (decremented) address specified in the modified data packet, modify the address of the data packet, and send the further modified data packet to the next ultrasound module 302 (e.g., module 70, not shown). This process may proceed until all the ultrasound modules 302 have their addresses set.

As a second example, in some embodiments the value of a given parameter may differ by ultrasound module 302 according to a particular function. For example, a delay value of a circuit component of the ultrasound modules 302 may differ according to a given function, such as a linearly increasing function. Although one manner of operation of the ultrasound probe is to send separate data packets with the differing delay values and an appropriate ultrasound module address for each data packet, an alternative is to send an initial data packet to a first ultrasound module 302 (e.g., module 72) of the ultrasound probe and have that ultrasound module operate on the data packet but also modify the data packet according to the function (e.g., the linearly increasing function) before sending the modified data packet to the next ultrasound module 302 in the chain (e.g., module 71).

The scenarios in which an ultrasound module 302 operates on a data packet but also modifies the data packet before sending it to a subsequent ultrasound module may be implemented by including suitable circuitry in the circuitry and ultrasound elements 408 of the ultrasound modules 302. For example, suitable digital logic may be included to perform the function(s).

The packets of data 304 may be provided to the ultrasound modules 302 via the respective shift register 402 of each ultrasound module 302. The decoder 406 of the ultrasound module 302 receiving the packet decodes the address from the packet and determines whether the address of the packet matches (or otherwise implicates) that specific ultrasound module 302. For example, the decoder 406 of the module 72 decodes the address of a received packet and determines whether the address identifies module 72. If so, then the data is provided to the circuitry and ultrasound elements 408 of that ultrasound module 302, which operate based on the data and provide resulting output data 409 from the multiplexer 404 of the ultrasound module 302. If, on the other hand, the address of the packet of data 304 does not implicate that specific ultrasound module 302 which received the packet as determined by the decoder 406 of that ultrasound module, then the data is shifted out of the shift register 402 directly to the multiplexer 404 and passed from the multiplexer 404 to the following ultrasound module 302 without the circuitry and ultrasound elements 408 of that particular ultrasound module acting on that data. For example, the module 72 may determine that a packet of data is not intended for module 72, and thus may provide the packet to the shift register of module 71 without acting on it. In this manner, the ultrasound modules 302 may perform a pass-through function in some situations depending on a control signal 410 provided by the decoder 406 to the multiplexer 404 of a given ultrasound module.

The modular nature of the ultrasound probe illustrated in FIGS. 3 and 4 simplifies scaling of the device in that similar or identical ultrasound modules 302 may be added to the daisy-chain without a need to re-design the majority of the signaling architecture. That is, the construction and signaling lines of ultrasound module 302 are the same for all the ultrasound modules, and thus may be designed at the ultrasound module level. In the embodiment of FIG. 4, only the clock signal 306 is provided separately (in parallel) to all the ultrasound modules 302 and thus is designed at the system level.

The ultrasound modules 302 (e.g., module 72, module 71 . . . module 1) may be identical even though they have different addresses in some embodiments to support address-based communication as described above. For example, in some embodiments, the address of an ultrasound module 302 is not hardwired into the circuitry but rather used to set a comparator register of the ultrasound module 302 which then compares the set address to the address in a received data packet to determine whether the data packet is addressed for that particular ultrasound module.

The use of a modular construction like that shown in FIGS. 3 and 4 also provides the benefit of simple verification. That is, verifying accurate operation of the ultrasound probe may be done at the module level rather than at the system level for most, if not all, functions of the ultrasound probe.

Also, it should be appreciated that the construction of ultrasound modules 302 allows for using the same shift register for input and output of data. Thus, more complex designs may be avoided.

Various structures may be used to load parameter data into programmable circuitry of an ultrasound probe. According to one aspect, dedicated hardware may be used. The hardware may be part of the ultrasound probe in at least some embodiments. For example, as described previously, an aspect of the present application provides an ultrasound probe having a parameter loader and a memory which stores parameter data for programming the programmable circuitry of the ultrasound probe, such as the programmable circuitry of ultrasound modules 302 described previously. FIG. 5 illustrates an example of circuitry which may be part of the ultrasound probe and which may include both a memory storing the parameter data as well as a parameter loader configured to control loading of the parameter data into the programmable circuitry. FIG. 5 represents an example in which the parameter loader and memory are part of an ASIC separate from the ultrasonic transducer array of the ultrasound probe, and thus represents a non-limiting example of an implementation of the ASIC 126 of FIG. 1B. However, it should be appreciated that the hardware performing the parameter loading functions may not be part of an ASIC in some embodiments. For example, a field programmable gate array (FPGA), or separate host may be used in some embodiments, among other examples.

The ASIC 500 of FIG. 5 includes a processor 502, a memory 503 for the processor 502, parameter loader 504 with memory 506, a host communication module 508 communicating (sending and receiving) signals 509 with a host (not shown), and an ultrasound element communication module 510. Coupled between the parameter loader 504 and the ultrasound element communication module 510 is a timing sequencer 514 having a multiplexer 516. The parameter loader 504 is configured as an input to the multiplexer 516, together with a trigger packet generator 518 and read packet generator 520. In this manner, the timing sequencer 514 can select whether to send parameter data, a trigger packet, or a read packet to the ultrasound element communication module 510 to be transferred to the ultrasound element chip (e.g., to the semiconductor die 112 in FIG. 1B). Data output by the ultrasound element chip and received by the ASIC 500 at ultrasound element communication module 510 may optionally be provided to a data p adder 530 and then to the host communication module 508 for communication to the host.

The ASIC 500 further comprises a sequence memory 512 storing sequences of acquisitions which may be performed and sequence processing unit queues 532 which stores information identifying which sequences in the sequence memory 512 are to be performed by the ultrasound probe. The ASIC 500 may also include a phase-locked loop (PLL) 522 which receives a clock input signal CLOCK and outputs a clock signal provided to various components of the ASIC 500. A reset control circuit 528 is included to control reset of the processor 502, and may be governed by a reset signal RESET provided over a bus 524. Communication among components of the ASIC 500 may be carried out over buses 524 and 526.

The processor 502 controls the functionality of the ASIC 500, including the operation of the parameter loader 504. To perform a desired imaging mode, a sequence of one or more acquisitions, stored in the sequence memory 512 and queued by the sequence processing unit queues 532, is performed. The acquisitions in turn may each specify the performance of one or more load records (also referred to herein simply as "loads"). The load records include pointers that reference the parameter data stored in the memory 506 of the parameter loader 504. The processor 502 configures and starts the parameter loader 504. Depending on the type of acquisition event being performed, the processor 502 may need to start the parameter loader 504 multiple times to complete loading of the necessary parameter data from the parameter loader 504 into the programmable circuitry of the ultrasound probe via the timing sequencer 514 and ultrasound element communication module 510.

The parameter loader 504 may be a hardware module operating in conjunction with handler state machines which handle the loading of parameter data from the parameter loader into the ultrasound element communication module 510 to be sent to the ultrasound modules of the ultrasound probe. The memory 506, which stores the parameter data for programming the programmable circuitry of the ultrasound probe (e.g., of the ultrasound modules 302), may be loaded initially by the host (e.g., host 204) via the host communication module 508 as part of signals 509. The data stored in the memory 506 may be raw binary data which may be loaded into the programmable circuitry of the ultrasound probe as is, in some embodiments, or which may be processed to generate desired configuration data in alternative embodiments. The parameter data stored in the memory 506 may be indexed, for example with pointers, and therefore need not be stored in a defined order or format in some embodiments.

The memory 506 may store, and the parameter loader 504 may load, parameter data relating to a variety of parameters depending on the programmable circuitry included in the ultrasound probe. The types of programmable circuitry depend, in some embodiments, on the desired functionality of the ultrasound probe, and thus the aspects of the present application are not limited to an ultrasound probe having any particular type of programmable circuitry. For example, if it is desired to provide flexibility in terms of the types of waveforms generated by the ultrasound probe, a programmable waveform generator may be provided. The exact type of waveform generator used is not limiting of the various aspects described herein. In some embodiments, programmable delay elements, or a programmable delay mesh (representing a network of multiple delay elements) may be provided to allow flexibility in setting the delay characteristics of the waveforms generated by the ultrasound probe. In some embodiments, variability in the receive functionality of the ultrasound probe may be desired, and thus programmable receive circuitry may be included, such as programmable ADCs, programmable filters and/or programmable modulators, among other possible examples. Non-limiting examples of programmable transmit and receive circuitry are described in connection with FIGS. 6 and 7 to illustrate the types of parameters for which parameter data may be stored in memory 506 of parameter loader 504.

The host communication module 508 provides communication of signals 509 between the ASIC 500 (and therefore the ultrasound probe of which the ASIC 500 is a part) and a host, such as host 204 of FIG. 2. As a non-limiting example, the host communication module 508 may be a USB bridge module when the ultrasound probe is coupled to the host via a USB connector, and the signals 509 may be of the type capable of being transferred over a USB connector.

The ultrasound element communication module 510 provides communication between the ASIC 500 and the ultrasound element chip (not pictured) including the ultrasound modules, such as ultrasound modules 302 previously described herein. Any suitable communication module may be provided as ultrasound element communication module 510, an example of which includes a low voltage differential signaling (LVDS) module. The communication may take the form of data 511 which may, for example, include data 304 and data out 307 described in connection with FIG. 3, among other possible types of data.

The timing sequencer 514 controls the timing of imaging activities performed by the ultrasound probe. The timing sequencer 514 includes a state machine in some embodiments and also includes a multiplexer 516 configured with three inputs. A state machine may be used to control the multiplexer 516 in terms of which input to the multiplexer is passed, and data may be streamed from the ASIC 500 to the ultrasound element chip. In some embodiments, the data may be streamed according to the Altera® Avalon Streaming specification (see Altera Corporation of San Jose, Calif.), although alternatives are possible. The trigger packet generator 518 generates a trigger packet which may be provided to the ultrasound element chip to trigger an imaging operation. The read packet generator 520 may be a state machine that generates the read request packets which control offload of data from the ultrasound modules of the ultrasound probe.

An example of the operation of the ASIC 500 is now described, although it should be appreciated that alternative manners of operation are possible. Initially, a reset signal RESET is provided to the reset control circuit 528 to cause a reset of the processor 502. One or more commands, included in signals 509, are then sent from the host (not shown in FIG. 5) via the host communication module 508 to the processor 502, instructing the processor 502 to perform a particular sequence stored in the sequence memory 512. The sequence processing unit queues 532 queues the selected sequence(s) from the sequence memory 512, which instructs the processor 502 on how to configure and operate the ultrasound element chip to perform the desired imaging operation. For instance, the load records of the sequence in sequence memory 512, which are accessed by the processor 502, include pointers that reference the parameter data stored in the memory 506 of the parameter loader 504. Based on the pointers of the load records, the processor 502 prompts the parameter loader 504 to generate the needed data packets with the parameter data. The implicated parameter data is then loaded into the programmable circuitry (e.g., on the ultrasound element chip) via the ultrasound element communication module 510 to operate the ultrasound probe. Examples of the parameter data are described further below. Data produced by and received from the ultrasound element chip is then provided to the ASIC 500 via the ultrasound element communication module 510 and then to the data padder 530 and host communication module 508 to be provided to the host.

Figure 6:
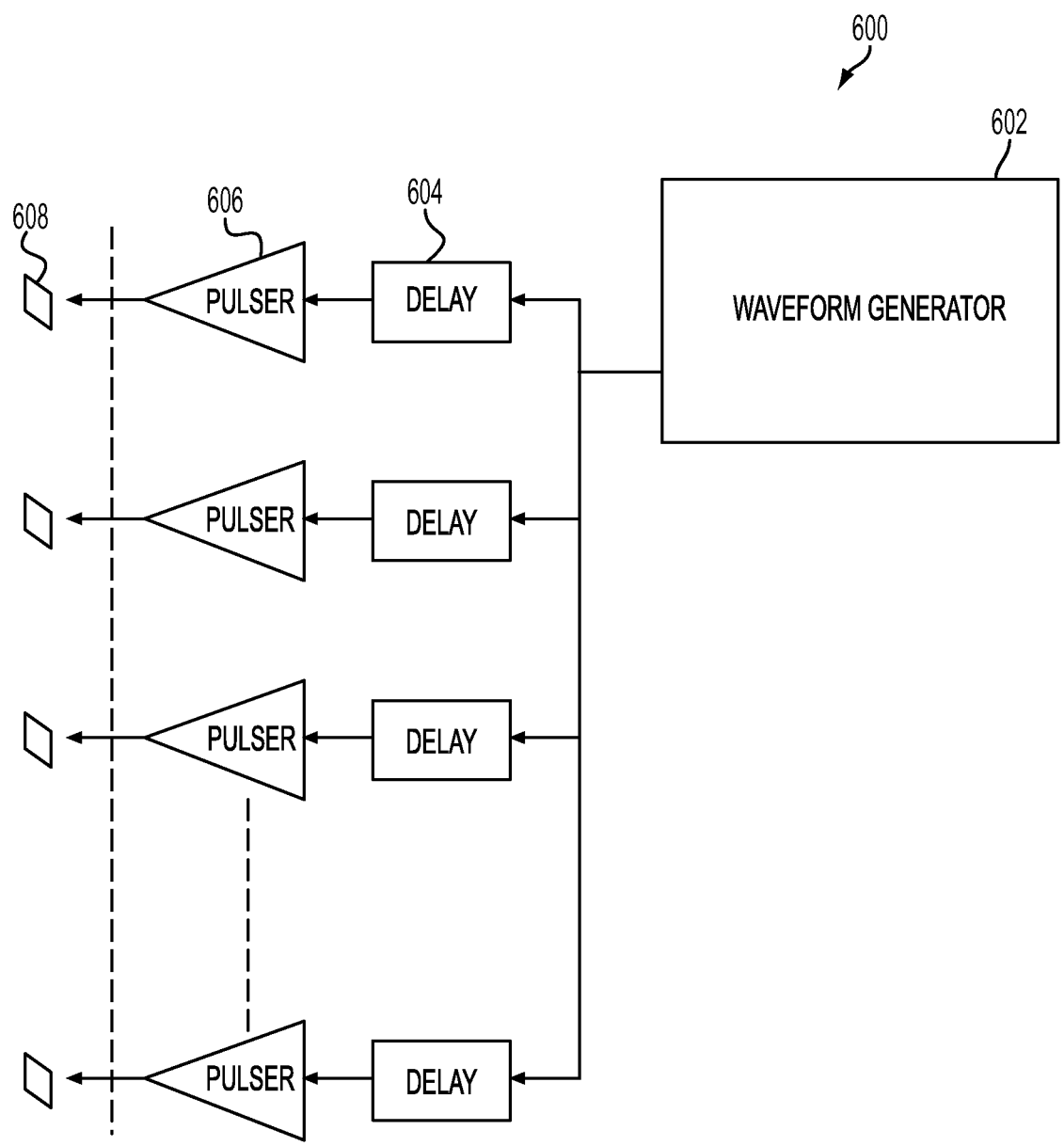
FIG. 6 illustrates an example of an ultrasound probe transmit channel including programmable circuitry which may be programmed by a parameter loader as described in connection with FIG. 5.

FIG. 6 illustrates in block diagram form an example of a transmit channel of an ultrasound probe including programmable components (e.g., the transmit circuitry 104). The transmit channel 600 includes a waveform generator 602, a delay element 604, a pulser 606, and an ultrasound element 608. One or more of these components may be programmable, such that operating the ultrasound probe may involve providing such components with parameter data. For example, the waveform generator 602 and/or delay element 604 may be programmable, as non-limiting examples. As a further specific example, the waveforms generated by the waveform generator 602 may be controlled in that, for example, the frequency, amplitude, phase, and/or rate of change of waveforms generated by the waveform generator 602 may be selected by setting registers of the waveform generator. Similarly, the delay elements 604 may be programmable. In the illustrated non-limiting embodiment of FIG. 6, the delay elements 604 each receive the waveform from the waveform generator 602, but in other embodiments the delay elements 604 may be coupled together, for example to form a delay mesh in which waveforms may be passed from one delay element to another. Operating features of the delay elements such as the amount of delay, which direction to pass a waveform (e.g., to a neighboring delay element on the right or a neighboring delay element on the left, forward, etc.), and whether to provide the waveform to a pulser may be programmed by setting parameter values of the delay elements.

Figure 7:
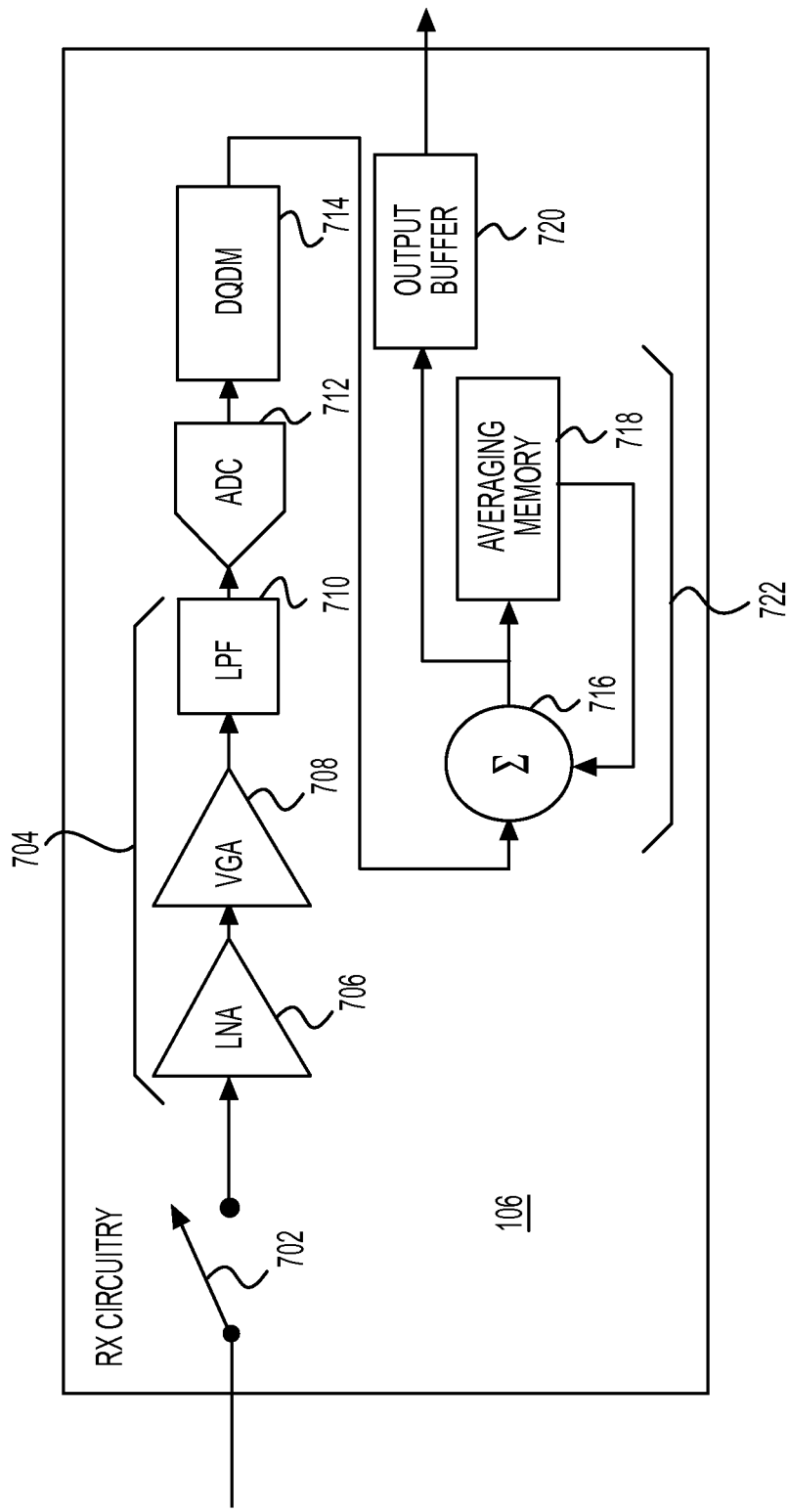
FIG. 7 illustrates an example of an ultrasound probe receive channel including programmable circuitry which may be programmed by a parameter loader as described in connection with FIG. 5.

FIG. 7 illustrates an example of the circuitry, both analog and digital, which may be included as part of a receive channel of an ultrasound probe (e.g., the receive circuitry 106). For example, the RX circuitry 106 and/or signal conditioning/processing circuitry 110 of FIG. 1A may include the components illustrated in FIG. 7. It should be appreciated that the components of FIG. 7 represent a non-limiting example, and that alternative components and arrangements may be implemented consistent with aspects of the present application.

As shown in FIG. 7, a receive control switch 702 may be provided and may be closed when the ultrasound probe is operating in a receive mode. An analog processing block 704 may be included, for example, with a low-noise amplifier (LNA) 706, a variable-gain amplifier (VGA) 708, and a low-pass filter (LPF) 710. In some embodiments, the VGA 708 may be adjusted, for example, via a time-gain compensation (TGC) circuit. The LPF 710 provides for anti-aliasing of the acquired signal. In some embodiments, the LPF 710 may, for example, comprise a 2nd order low-pass filter having a frequency cutoff on the order of 5 MHz. However, other implementations are possible and contemplated.

The receive circuitry may also include an ADC 712. The ADC 712 may be, for example, a 10-bit, 12-bit, 20 Msps, 40 Msps, 50 Msps, or 80 Msps ADC.

The receive circuitry may also include digital circuitry in some non-limiting embodiments, including the embodiment of FIG. 7. As shown, a digital quadrature demodulation (DQDM) circuit 714, an accumulator 716, an averaging memory 718, and an output buffer 720 may be included. The accumulator 716 and averaging memory 718 together may form an averaging circuit 722.

The DQDM circuit 714 may, for example, be configured to mix down the digitized version of the received signal from center frequency to baseband, and then low-pass filter and decimate the baseband signal. The DQDM 714 may, for example, include a mixer block, a low-pass filter (LPF), and a decimator circuit. The illustrated circuit may allow for a lossless (or lossy) reduction of bandwidth by removing frequencies from the received signal, thus significantly reducing the amount of digital data that needs to be processed by the signal conditioning/processing circuit 110 and offloaded from the die 112.

While programmable circuitry components have been described in connection with FIGS. 6 and 7 with respect to the transmit and receive functionality of the ultrasound probe, it should be appreciated that ultrasound probes to which aspects of the present application may apply may additionally include programmable circuitry which is not specific to transmit or receive functions of the ultrasound probe. For example, timing circuitry and general control circuitry (e.g., timing and control circuit 108) may also be part of the ultrasound probe and may include one or more programmable features. Thus, the memory 506 may store and the parameter loader 504 may load parameter data related to these other types of circuitry as well.

It should be appreciated from the foregoing discussion that ultrasound probes may include various circuitry (analog and digital) and therefore that various parameters may be needed to program a given ultrasound probe depending on which circuit components are included in that probe and what mode of operation is being performed. For clarity, a brief summary of non-limiting examples of parameters for which parameter data may be stored and loaded on an ultrasound probe is now provided.

In some embodiments, an ultrasound probe may include a programmable waveform generator. Programming the waveform generator may involve specifying one or more of the following: waveform delay; waveform amplitude; waveform duration (total length of waveform); waveform envelope; initial phase of the waveform; initial frequency of the waveform; chirp rate (if a chirp is to be generated); invert bit (to invert the waveform); and coded-excitation (a bit enabling shifting of the chirp rate parameter for use with a coded-excitation).

In some embodiments, a programmable delay element or delay mesh may be provided as part of an ultrasound probe. The types of programmable features will depend on the specific type of programmable delay element used. For purposes of illustration, it can be assumed that the delay element is coupled to a pulser and includes a buffer or other memory with multiple storage locations. In this case, examples of programmable features of a delay element may include: write select, to select to which location of the delay element memory to write data; read select to select from which location of the delay element memory to read data; pulser enable (to enable a pulser to which the delay element may be coupled); delay element enable (to enable or disable the delay element itself); and an invert bit (to invert the signal (e.g., waveform) being delayed by the delay element).

Components which operate as part of the receive functionality of an ultrasound probe may also be programmable. For example, as described previously, an ultrasound probe may include a DQDM module, a LPF, a data averaging block, and a sample memory. Parameters associated with one or more such components may be set. For example, with respect to the data averaging block, parameters such as bit shift, word extend, and accumulate may be set. Variable bit-width memory packing of the memory may also be set.

As previously described in connection with FIG. 5, an ultrasound probe may include a sequencer (e.g., timing sequencer 514), which may at least partially control timing of the operation of the ultrasound probe. Examples of sequencer timing values which may be programmable include: time at which a trigger packet is sent; time at which the first read packet is sent; the time at which the processor (e.g., processor 502 of ASIC 500) is interrupted to begin generating parameter data for the next acquisition; the time at which an acquisition should end and the counter should be reset (e.g., to zero); and the time at which the parameter loader (e.g., parameter loader 504) should complete generating the parameter data.

The examples of parameters described above are not limiting in that various aspects of the present application may apply whether those specific components and/or parameters are implicated by a particular ultrasound probe or not. Also, alternative or additional circuitry and parameters may be used in other embodiments.

Operating programmable ultrasound probes may involve setting of a large number of parameters, as should be appreciated from the foregoing discussion. For example, fully specifying operation of the ultrasound probe may involve setting multiple (e.g., more than five, more than 10, more than 50, more than 100, between 5 and 200, or any other suitable number) parameters for each of the ultrasound modules 302. Considering that an ultrasound probe may include many such modules as described in connection with FIG. 3, the result may be that thousands of parameter values need to be specified for the ultrasound probe. Compound that further by provision for operation in multiple different imaging modes which may require setting of different parameter values, and the number of parameters and parameter values may pose a challenge in terms of the ability to send the parameter values to the ultrasound probe from a host in a timely manner and/or the ability to individually store all the needed parameter data in the memory of the parameter loader. Thus, aspects of the present application are directed to techniques for reducing the amount of parameter data to be transferred from a host to an ultrasound probe and for reducing the amount of parameter data to be stored on the ultrasound probe and loaded into the programmable circuitry.

According to an aspect of the present application, at least some parameter data may be designated and treated as global data to be provided to all ultrasound modules of the ultrasound probe. As used herein, global parameter data is that data which is the same for all modules of the ultrasound probe, while local parameter data is parameter data specific to a module, and which therefore may differ from the parameter data required by a different module for the same parameter. Treating certain parameter data as global data may reduce the amount of parameter data to be generated and loaded into the programmable circuitry of the ultrasound probe. An example is described now in the context of a waveform generator of an ultrasound probe, although the distinction between global and local parameter data and the use of global parameter data to reduce data generation and storage requirements may apply to other programmable circuitry of the ultrasound probe.

For purposes of illustration, it is assumed that each waveform generator of the ultrasound probe (e.g., two waveform generators per ultrasound module 302) can be programmed with respect to the following parameters: waveform delay; waveform amplitude; waveform duration (total length of waveform); waveform envelope; initial phase of the waveform; initial frequency of the waveform; chirp rate (if a chirp is to be generated); invert bit (to invert the waveform); and coded-excitation (a bit enabling shifting of the chirp rate parameter for use with a coded-excitation). For at least some imaging modes, many such parameters may have the same value for all the waveform generators. For example, in some modes, such as some forms of B-mode imaging, all the parameters may be global except for the delay parameter, which may have a separate value for each ultrasound module or for each waveform generator in each ultrasound module. An example of such a mode of operation is a two-dimensional (2D) imaging mode, although other modes may be the same in this respect. In some modes, all the parameters may have a global value except for the delay parameter and the waveform amplitude parameter, which may vary by ultrasound module. An example of such a mode is a 2D imaging mode with apodization. In some modes, the delay value, initial frequency, and initial phase may differ by ultrasound module while the remaining waveform generator parameters may be the same for all ultrasound modules. In such modes, adjustment of the initial frequency and phase may provide fine control of the delay, and thus such modes may be considered "fine delay" modes.

According to an aspect of the present application, a parameter loader of an ultrasound probe, such as parameter loader 504, may generate and send global parameters from its internal memory (e.g., memory 506), while local parameters may be read sequentially from the sequence memory of the ultrasound probe (e.g., sequence memory 512). In this manner, the parameter data stored by the memory 506 and loaded by the parameter loader 504 may be less than if separate parameter values were generated for each ultrasound module 302 even for global parameters. As the number of global parameters increases, the data savings increases as well.

As an example, in the fine delay mode, parameters such as waveform amplitude, chirp rate, waveform length, whether to invert the waveform, and whether a coded-excitation is to be generated may have global values. By contrast, the waveform delay parameter, initial waveform phase parameter, and initial frequency parameter may have local values, which differ by ultrasound element. In some embodiments, the parameter loader (e.g., parameter loader 504) may read the global values from its internal memory (e.g., memory 506) and send those to the ultrasound elements of the ultrasound probe. Subsequently, the parameter loader may generate and send, to the ultrasound modules, packets which are addressed to specific ultrasound modules and include the local parameter values for those ultrasound modules.

While some parameters may have local values or global values, in some embodiments a given parameter may have the same value for all but one ultrasound module of the ultrasound probe. In such embodiments, a data packet for that given parameter may specify all ultrasound modules except for one. Thus, only the one ultrasound module not specified may fail to operate on the data packet. Further still, in some embodiments a packet may be intended for a group of ultrasound modules. In such scenarios, the packet may specify a range of addresses of ultrasound modules, for example by including both a start address and an end address. The ultrasound modules having addresses falling with the range defined by the start address and end address may operate on the packet. To determine whether or not the packet is intended for a given module, that module may include suitable circuitry to compare its own module address to the range specified by the packet. Such circuitry may be included in the circuitry and ultrasound elements 408 of the ultrasound modules 302 shown in FIG. 4. Such circuitry may include, for example, suitable digital logic. This manner of operation in which a packet addresses a plurality, but not all, ultrasound modules may be particularly beneficial in ultrasound probes having a large number of ultrasound modules.

As previously described, in some embodiments the values of two or more parameters may be grouped into a single data packet, and thus the packet may include only global parameters, only local parameters, or a combination of global and local parameters. As an example, assuming an ultrasound probe with programmable waveform generators which can be programmed to control, among other features, the waveform delay, whether the waveform generated is a coded excitation, and whether to invert the waveform, the values for such parameters may be grouped into a common data packet. This may be done, for example, to facilitate efficient system operation. For instance, assuming further that the waveform delay value is specified using 14 bits, the coded excitation control is specified with a single bit, and the control over whether to invert the waveform is specified with a single bit, a single 16-bit packet may be generated to include all three values as compared to having to create unique packets for each of these three parameters. Thus, the system may be simplified compared to a scheme in which unique packet types are generated for each parameter, a simplification which may increase in significance as the number of parameters increases. With the simplification comes a decrease in flexibility, since having unique packet types for each parameter may allow greater control over exactly what data is generated and transmitted.

In some embodiments in which multiple parameters are grouped into a common packet, the grouping may be based on common function. Considering the example of the waveform generator delay, the coded excitation control, and the waveform inversion control just described, those three parameters share the common function of programming the waveform generator. However, the method of operating an ultrasound probe by grouping together two or more parameters into a common packet is not limited to grouping parameters with a common function.

The foregoing example also illustrates how a data packet may include both local and global parameters. Considering the example described above in which 2D imaging is performed with an ultrasound probe and the waveform generator parameters are the same for all ultrasound modules except for a difference in waveform delay, use of a single packet type to transfer parameter values for the waveform delay, the invert bit, and the coded-excitation bit would represent a scenario in which the packet includes global parameters (the invert bit and the coded-excitation bit) and a local parameter (the waveform delay).

According to an aspect of the present application, savings in parameter data generation and storage may be realized by taking advantage of the characteristics of particular modes of operation of the ultrasound probe. As an example, according to an aspect of the present application, a mode of operation of the ultrasound probe allows for specifying identical waveforms for all the ultrasound elements within a column. For example, the ultrasound probe may be used with an acoustic lens which may provide focusing in an elevation direction of the ultrasound beam. Thus, the ultrasound elements within a column may transmit identical waveforms, which allows for specifying fewer parameter values for the ultrasound module including those ultrasound elements. For example, assuming an ultrasound array size as described in connection with FIG. 3, sixty-four times fewer unique configuration parameters may be required to fully specify operation of the ultrasound probe compared to if the ultrasound elements within columns of the ultrasound modules are used to generate different waveforms. More specifically, and as a non-limiting example, delay mesh parameters may be defined for two adjoining 2×32 modules (e.g., two modules 302 of FIG. 3 arranged in a left-to-right configuration with respect to each other in FIG. 3), and then repeated for all such 72 adjoining modules, leading to a significant reduction in needed parameter data.

According to an aspect of the present application, the number of parameter values stored by the parameter loader (e.g., parameter loader 107 or 504) is reduced by implementing a scheme in which the parameter values are generated using indices of the columns and rows of the ultrasound transducer array. For example, for some imaging modes, such as a B-mode or a Doppler mode in which all the circuitry parameters may have a global value except for the delay parameter and the waveform amplitude parameter, the values of a particular parameter may differ by column and by row of the ultrasound transducer array in a manner in which the variation by column is separable from the variation by row. In such situations, each row and each column may be assigned a value for that given parameter, and the value of the parameter for a specific ultrasound element may be computed by suitably combining the value for the row and the value for the column.

As a non-limiting example, waveform delay values $\tau$ may be specified for the columns and rows of the ultrasound transducer array, and the waveform delay value $\tau$ for a given ultrasound element may be specified by a summation of the waveform delay value for the row and the waveform delay value for the column. For example, the waveform delay value for an ultrasound element positioned at row 5, column 108 may be equal to $\tau_5+\tau_{108}$ where $\tau_5$ is the waveform delay for row 5 and $\tau_{108}$ is the waveform delay for column 108.

While a summation is one example of a combination, other manners of combining the values may be used, such as multiplication. For instance, waveform amplitude values may be specified for rows and columns of the ultrasound transducer array and the waveform amplitude for a given ultrasound element may be the product of multiplying the waveform amplitude for that row by the waveform amplitude for that column. As a specific example, the waveform amplitude for an ultrasound element positioned at row 5, column 108 may be equal to $A_5 A_{108}$, where $A_5$ is the waveform amplitude assigned to row 5 and $A_{108}$ is the waveform amplitude assigned to column 108.

Using these manners of generating parameter data from a reduced set of indexed parameter data values, the parameter loader may store less parameter data than if a parameter value was to be stored for every ultrasound element of the ultrasound probe. The cost, however, is that the parameter loader in such embodiments should include suitable circuitry to perform the combination function, such as adder circuitry, multiplication circuitry, etc. Other examples of manners of combining indexed parameter data values include logic functions, such as OR and XOR functions. Suitable circuitry may be included to perform such functions where desired.

Aspects of the present application also provide for a reduction in parameter data across multiple events. To form a single ultrasound image frame, multiple events are typically performed. Each event may, in some embodiments, involve a unique parameter data set. Thus, the greater the number of events performed the greater the parameter data needed. However, Applicant has recognized that redundancies in parameter data values exist across events in at least some imaging modes, and that such redundancies may be utilized to reduce the amount of parameter data required to be generated and stored by the parameter loader of the ultrasound probe.

One such example occurs when delays are shifted between events. For example, in imaging modes such as B-Mode focused scanning the configuration parameters for a particular ultrasound element (or, alternatively, an ultrasound module) during a particular event may be the same as at least some of the configuration parameters for a different ultrasound element (or ultrasound module) one or more events prior. That is, the waveform delay generated by the ultrasound probe may be propagated or laterally shifted along the ultrasound elements of the ultrasound probe. Thus, according to an embodiment of the application, a set of parameter data that may be longer than that needed to specify a single event may be stored in the sequence memory and the parameter loader may start at a different offset within the sequence memory when executing subsequent events.

According to an aspect of the present application, one or more counters are included in the ultrasound probe to facilitate reducing the amount of parameter data generated and stored. For example, a linear counter, such as a 10-bit counter, may be included in the parameter loader and may calculate the waveform delay values for generation of plane waves. The counter may increment after each ultrasound element position to calculate the appropriate delay values. In this manner, the delay values need not be stored in the memory of the parameter loader (e.g., memory 506). Such operation may be performed when generating plane waves in the azimuth direction. Similarly, a linear counter may be used for the lateral direction to set the read and write parameters of an ultrasound module.

Counters may also be used in the context of generating three-dimensional plane waves. For example, in addition to the linear counter described above, a second counter may be included to define a plane wave slope. This second counter may increment after each ultrasound module (or other configuration unit) and may, for example, be reset after a given number of configuration units, such as after every 16 configuration units. The delay value for the plane wave may be the sum of the values from the two counters. In some embodiments, one or more of the counters may include fractional bits, for example to allow for finer delay steps to be specified. These finer delays may be truncated or rounded in some embodiments. Moreover, it should be appreciated that counters represent a non-limiting example of a manner of calculating the delays. Alternatives include the use of a central processing unit (CPU) or an arithmetic logic unit (ALU).

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application allow for storage of parameter data on an ultrasound probe distinct from a host. The parameter data may be efficiently and accurately loaded into digital programmable circuitry of the ultrasound probe using a parameter loader on the ultrasound probe. The parameter data may be efficiently conveyed to relevant ultrasound modules of the ultrasound probe using addressable packet-based communication, and the ultrasound modules may be coupled together to facilitate sharing of the parameter data. Also, the amount of parameter data generated and stored on the ultrasound probe may be reduced by taking advantage of various aspects described herein.

Ultrasound probes according to aspects of the present application may be easily scalable and allow for simple verification of operation. For instance, aspects have been described in which (at least some of) the circuitry of the ultrasound probe is grouped into repeatable modules. Thus, the ultrasound probes may be scaled easily by adding additional identical modules, without requiring significant re-design at the system level. Also, verification of operation of the ultrasound probe may be performed substantially at the module level in such scenarios.

The power requirements of the ultrasound probe may also be reduced compared to alternative probe designs. For example, use of ultrasound modules configured into arrays (e.g., chains, such as a daisy-chain) may allow for fewer wires between modules than if a multiplexer-based approaches were used, thus allowing for reduction in power. Similarly, the use of global packet distribution as described herein may be more efficient than multiplexer-based designs.

The area consumed by the ultrasound modules may also be relatively small according to aspects of the present application. For example, some embodiments described herein include ultrasound modules having a number of registers which scales linearly with the number of ultrasound modules. By contrast, if multiplexer-based designs were to be utilized, the number of registers involved may be much greater, for example scaling quadratically with the number of ultrasound modules.

Aspects of the timing operation of the ultrasound probe may also be simplified compared to alternatives. For example, timing of operation of the ultrasound modules may be synchronized within the ultrasound modules. Such a scheme may avoid the need for any global trigger wires.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers. In some embodiments, the processors described herein may be virtual processors.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus, comprising:
   an ultrasound probe, comprising:
      a plurality of modules including a first module and a second module, wherein each of the first and second modules comprises transmit circuitry, at least one ultrasound element comprising an ultrasonic transducer, and receive circuitry, and wherein the transmit circuitry is configured to control transmit operations of the ultrasonic transducer and the receive circuitry is configured to control receive operations of the ultrasonic transducer;

a memory configured to store digital parameter data including control data of the transmit circuitry and control data of the receive circuitry of the first and second modules; and a parameter loader coupling the memory to the first and second modules;

wherein the parameter loader is configured to provide the control data of the transmit circuitry and the control data of the receive circuitry of the first and second modules from the memory to the first module, and wherein the first module and second module are coupled to each other and the first module is configured to pass the control data of the transmit circuitry and the control data of the receive circuitry of the second module to the second module.

2. The apparatus of claim 1, wherein the parameter loader and memory are disposed on a first substrate, and wherein the first module and second module are disposed on a second substrate coupled to the first substrate.

3. The apparatus of claim 2, wherein the parameter loader comprises a linear counter.

4. The apparatus of claim 1, wherein the apparatus further comprises a host coupled to the ultrasound probe by a cable.

5. The apparatus of claim 1, wherein the apparatus further comprises a host coupled to the ultrasound probe by a wireless connection.

6. The apparatus of claim 1, wherein the transmit circuitry of the first module comprises a waveform generator and/or delay mesh circuitry, and wherein the digital parameter data includes waveform generator data and/or delay mesh circuitry data.

7. The apparatus of claim 1, wherein each of the first and second modules includes a decoder configured to receive a packet of information and decode an address from the packet of information.

8. The apparatus of claim 7, wherein the first module is configured to operate on the packet of information only if the address identifies the first module.

9. The apparatus of claim 7, wherein the first module is configured to pass the packet of information to the second module without operating on the packet if the address does not identify the first module.

10. The apparatus of claim 7, wherein the first module is configured to modify the packet of information and send it to the second module.

11. A method of providing digital data to an ultrasound probe, the ultrasound probe comprising a plurality of addressable ultrasound modules linked in a daisy-chain configuration, the plurality of addressable ultrasound modules including a first ultrasound module and a second ultrasound module, wherein each of the first and second ultrasound modules comprises at least one ultrasound element comprising an ultrasonic transducer, transmit circuitry, and receive circuitry, wherein the transmit circuitry is configured to control transmit operations of the ultrasonic transducer and the receive circuitry is configured to control receive operations of the ultrasonic transducer, the method comprising:

creating a packet including both an address of one of the plurality of addressable ultrasound modules and digital data, wherein the digital data comprises control data of the transmit circuitry and control data of the receive circuitry of the one of the plurality of addressable ultrasound modules;

sending the packet to the first ultrasound module; and using the first ultrasound module of the plurality of addressable ultrasound modules to decode the address from the packet.

12. The method of claim 11, wherein the one of the plurality of addressable ultrasound modules is the first ultrasound module, the method further comprising using the first ultrasound module to operate on the digital data of the packet.

13. The method of claim 11, further comprising modifying the packet with the first ultrasound module prior to sending the packet from the first ultrasound module to the second ultrasound module of the plurality of addressable ultrasound modules.

14. The method of claim 13, wherein modifying the packet comprises altering the address.

15. The method of claim 11, further comprising sending the packet to the second ultrasound module of the plurality of addressable ultrasound modules prior to sending the packet to the first ultrasound module, and subsequently sending the packet from the second ultrasound module to the first ultrasound module.

16. The method of claim 15, further comprising decoding the address with the second ultrasound module and not operating on the digital data of the packet with the second ultrasound module.

17. The method of claim 11, further comprising receiving the packet with a shift register of the first ultrasound module of the plurality of addressable ultrasound modules and outputting the packet from the shift register of the first ultrasound module to a shift register of the second ultrasound module of the plurality of addressable ultrasound modules.

18. The method of claim 11, wherein creating the packet including the address of the one of the plurality of addressable ultrasound modules comprises creating the packet to include an address specifying all but one ultrasound module of the plurality of addressable ultrasound modules.

19. The method of claim 11, wherein creating the packet including the address of the one of the plurality of addressable ultrasound modules comprises creating the packet to include an address range specifying multiple, but not all, ultrasound modules of the plurality of addressable ultrasound modules.

* * * * *

UNITED STATES PATENT AND TRADEMARK OFFICE
CERTIFICATE OF CORRECTION

| | | |
|---|---|---|
| PATENT NO. | : 11,137,486 B2 | Page 1 of 1 |
| APPLICATION NO. | : 15/517211 | |
| DATED | : October 5, 2021 | |
| INVENTOR(S) | : Ralston et al. | |

It is certified that error appears in the above-identified patent and that said Letters Patent is hereby corrected as shown below:

On the Title Page

Item (71), Applicant, please change the text:
Butterfly Network, Inc., Guilford, CT (US)
To:
--BFLY Operations, Inc., Guilford, CT (US)--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*